United States Patent [19]

Opitz et al.

[11] Patent Number: 4,628,062
[45] Date of Patent: Dec. 9, 1986

[54] 1,4-NAPHTHOQUINONE DERIVATIVES HAVING ANTI-INFLAMMATORY ACTION

[75] Inventors: Wolfgang Opitz, Overath; Bernhard Pelster, St. Augustin; Romanis Fruchtmann, Cologne; Udo Krupka, Marburg; Walter Gauss, Cologne; Hartmut Kiehne, Odenthal; Hermann Oediger, Cologne, all of Fed. Rep. of Germany

[73] Assignee: Troponwerke GmbH & Co., KG, Cologne, Fed. Rep. of Germany

[21] Appl. No.: 682,408

[22] Filed: Dec. 17, 1984

[30] Foreign Application Priority Data

Dec. 31, 1983 [DE]  Fed. Rep. of Germany ....... 3347658

[51] Int. Cl.⁴ .................. A61K 31/12; C07C 50/14; C07C 97/22
[52] U.S. Cl. .................. 514/569; 260/396 R; 514/603; 514/616; 514/618; 514/629; 514/657; 514/682
[58] Field of Search .................. 260/396 R; 514/682, 514/603, 657, 629, 569, 618, 616

[56] References Cited

U.S. PATENT DOCUMENTS 3,070,492 12/1962 Rapport .................. 260/396 R
4,110,473 8/1978 Fugitt et al. .................. 424/331

FOREIGN PATENT DOCUMENTS 0007985 2/1980 European Pat. Off. .
2456655 7/1975 Fed. Rep. of Germany .

OTHER PUBLICATIONS

Chemical Abstracts, vol. 100, No. 2, dated 1/9/84, Chemistry of Synthetic High Polymers, pp. 376–377.
Chemical Abstracts, vol. 59, No. 6, dated 9/16/63, Condensed Aromatic Compounds, pp. 6325–6327.
Chemical Abstracts, vol. 59, No. 3, dated 8/5/63, Condensed Aromatic Compounds, p. 2733.
Chemical Abstracts, vol. 49, No. 22, dated 11/25/55, p. 16047.
Chemical Abstracts, vol. 45, No. 15, dated 8/10/51, p. 6801.
Winter et al., Proc. Soc. Exp. Biol. Med., 111, 544 (1962).
Brune et al., Naunyn-Schmeideberg's Arch. Pharmacol., 315, 269 (1981).
Borgeat et al., Proc. Natl. Acad. Sci., USA, 76, 2,148 (1979).
Ford-Hutchinson et al., Brit. J. Pharmacol., 76, 215 (1982).
Cunningham et al., Agents & Actions, 11, 583 (1981).

*Primary Examiner*—Richard L. Raymond
*Assistant Examiner*—Raymond Covington
*Attorney, Agent, or Firm*—Sprung Horn Kramer & Woods

[57] ABSTRACT

New compounds of the formula

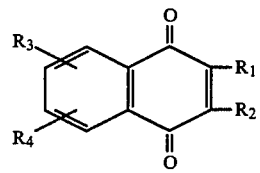

in which
$R_1$ is an allylamino, acetylamino or propionylamino radical,
$R_2$ is hydrogen or a 2-methoxyethoxy or ethoxy radical,
$R_3$ is hydrogen or a sulphamoyl radical, and
$R_4$ is hydrogen, and of the formula

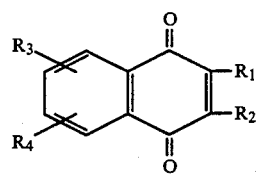

in which
$R_1$ is a halogen atom or a free or substituted hydroxyl, sulphhydryl or amino group,
$R_2$ is a hydrogen atom, an alkyl radical, a halogen atom, or a free or substituted hydroxyl, sulphhydryl or amino group,
$R_3$ and $R_4$ each independently is hydrogen, alkyl, hydroxyl, alkoxy, sulphonamido or halogen, with the proviso that $R_2$, $R_3$ and $R_4$ are hydrogen when $R_1$ is hydroxyl, exhibit anti-inflammatory activity.

15 Claims, No Drawings

1,4-NAPHTHOQUINONE DERIVATIVES HAVING ANTI-INFLAMMATORY ACTION

The present invention relates to naphthoquinone derivatives and to their use as active components in anti-inflammatory medicaments. The naphthoquinone derivatives correspond to the general formula I

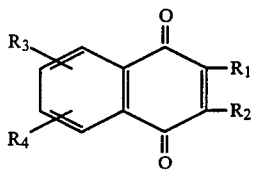

in which
$R_1$ can represent a halogen atom or a free or substituted hydroxyl, sulphhydryl or amino group,
$R_2$ can have the same meaning as $R_1$ and be identical to or different from the latter or can represent an alkyl radical or a hydrogen atom, and
$R_3$ and $R_4$, which can be identical or different, can represent hydrogen and alkyl, hydroxyl, alkoxy, sulphonamido and halogen substituents, with the proviso that $R_2$, $R_3$ and $R_4$ denote hydrogen when $R_1$ is hydroxyl.

It has been found, surprisingly, that the compounds, of the general formula I, on which the present invention is based have superior actions in respect of their anti-inflammatory and antiarthritic actions, since they have excellent anti-inflammatory and antiarthritic effects and low general toxicity in all customary forms for administration.

The present invention also relates to compounds of the general formula II

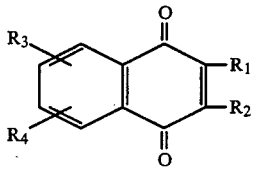

in which
$R_1$ denotes an allylamino, acetylamino or propionylamino radical,
$R_2$ denotes hydrogen or a 2-methoxyethoxy or ethoxy radical,
$R_3$ denotes hydrogen or a sulphamoyl radical, and
$R_4$ denotes hydrogen.

Preferred compounds of the general formula II are 2-allylamino-6-sulphamoyl-1,4-naphthoquinone, 2-propionylamino-3-(2-methoxyethoxy)-1,4-naphthoquinone and 2-acetylamino-3-ethoxy-1,4-naphthoquinone.

The invention also relates to agents containing one or more of the compounds of the general formula II above or particularly of the 3 above mentioned compounds, and to the use of these 3 compounds or the abovementioned compounds of the general formula II for combating diseases, preferably for combating inflammations.

The compounds of the general formula I which are preferred are those in which
$R_1$ can represent a hydroxyl group, an alkoxy group having one to two C atoms, which can be substituted by a methoxy group, or a carboxymethylmercapto group and alkylamide and hydroxylalkylamide derivatives derived therefrom, their alkyl radicals containing up to three C atoms, or a free or a saturated or unsaturated monoalkylamino group having up to 13 C atoms which can be substituted by a hydroxyl or an acetoxy group, or a phenylamino group which can be substituted by one or two halogen atoms, preferably chlorine atoms, or methoxy, nitro, carboxyl or sulphamoyl group, or an acetylamino or propionylamino group or a chlorine atom,
$R_2$ can have the same meaning as $R_1$ and be identical to or different from the latter, or can represent a methyl or ethyl group or a hydrogen atom, and
$R_3$ and $R_4$, which can be identical or different, can represent hydrogen and $C_1$–$C_4$-alkyl, hydroxyl, $C_1$–$C_4$-alkoxy, sulphonamido or halogen substituents.

Particularly preferred compounds of the general formula I, in which $R_1$–$R_4$ have the abovementioned meaning, are:

2-hydroxy-1,4-naphthoquinone

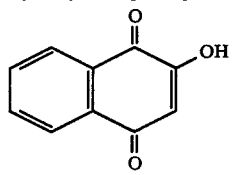

Compound 1

2-methoxy-1,4-naphthoquinone

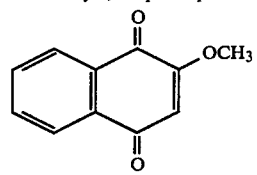

Compound 2

2-(2-methoxyethoxy)-1,4-naphthoquinone

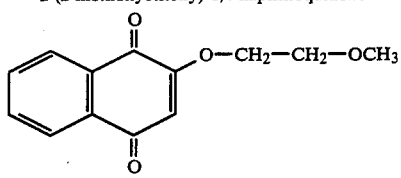

Compound 3

2,3-dimethoxy-1,4-naphthoquinone

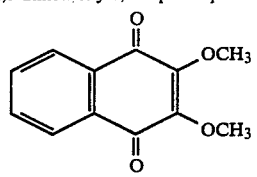

Compound 4

2-amino-1,4-naphthoquinone

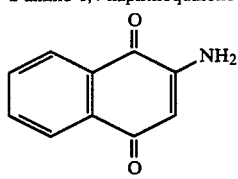

Compound 5

2-amino-6-sulphamoyl-1,4-naphthoquinone

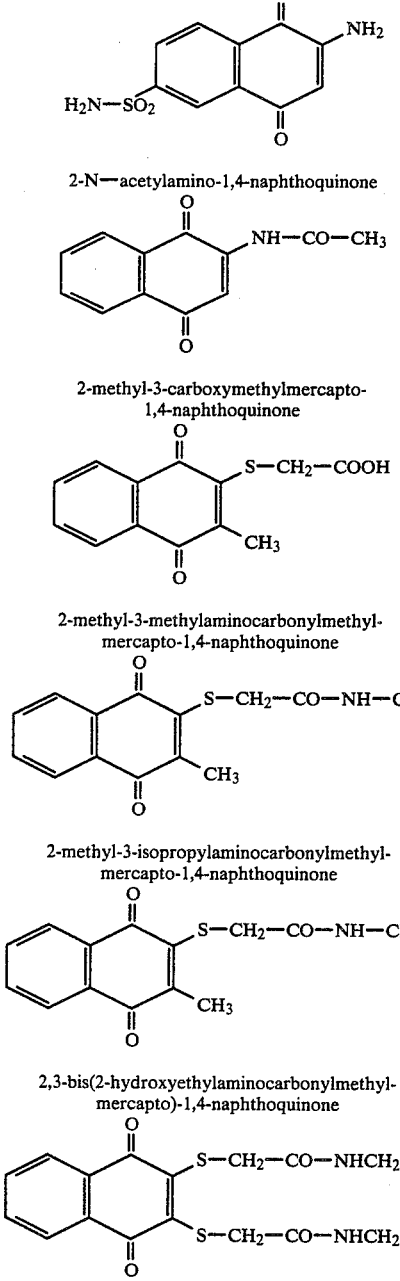

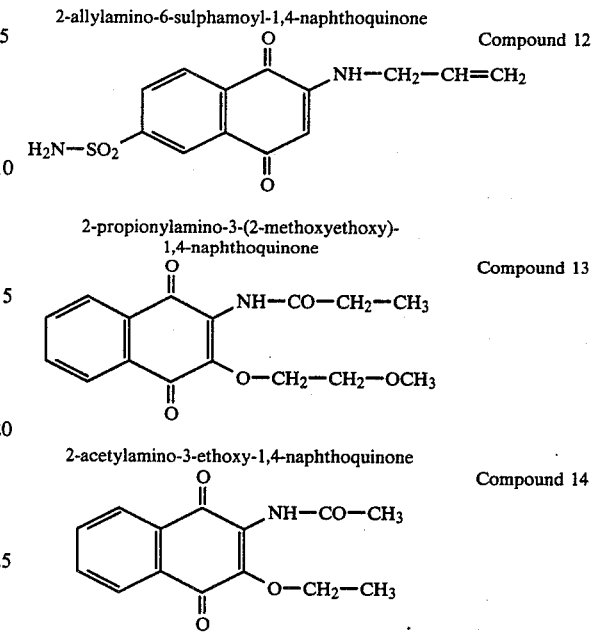

as well as the compounds listed below, which have not hitherto been described and as such are particularly preferred according to the invention. Also the use of these compounds for combating diseases, in particular for inhibiting inflammation, is preferred according to the invention. The same applies to their use in or as agents for use for combating diseases, in particular inflammations.

The compounds of the general formulae I and II strongly inhibit the oedema induced by carrageenan in the rat paw. This was demonstrated by the method of Winter et al., Proc. Soc. Exp. Biol. Med. 111, 544 (1962), with the modification that, to induce oedema, pure λ-carrageenan was used in the form of a 0.25% suspension in physiological saline solution (Tab. 1, column 1).

The compounds of the general formulae I and II inhibit the metalolism of arachidonic acid via the cyclooxygenase route. (Method of Brune et al., Naunyn-Schmeideberg's Arch. Pharmacol. 315, 269 (1981)) (Tab. 1, column 2).

Surprisingly, in addition all the compounds of the general formula I and II also extremely strongly inhibit the metabolism of arachidonic acid via the lipoxygenase route (Tab. 1, column 3).

The method of measurement is based on the determination of the release of $LTB_4$ from neutrophilic granulocytes (PMN) of the rat after stimulation with Ca ionophor, using reverse phase HPLC (Borgeat et al., Proc. Natl. Acad. Sci. USA 76, 2,148 (1979), Ford-Hutchinson et al., Brit. J. Pharmacol. 76, 215 (1982).

Furthermore, it has been demonstrated for compounds of the general formulae I and II that they inhibit the aggregation of PMN stimulated by $LTB_4$, which has chemotactic effects, and thus contribute to the anti-inflammatory action (method of Cunningham et al., Agents & Actions 11, 583 (1981)) Tab. 1, column 4).

TABLE 1

| Compound | Column 1<br>% inhibition of carrageenan oedema at 2.5 mg/kg orally | Column 2<br>% inhibition of cyclooxygenase at $1 \times 10^{-5}$ mol/l | Column 3<br>% inhibition of lipoxygenase at $1 \times 10^{-5}$ mol/l | Column 4<br>% inhibition of aggregation of PMN at $1 \times 10^{-4}$ mol/l |
|---|---|---|---|---|
| 1 | 34 | 31 | 70 | |
| 2 | 29 | 78 | 98 | 76 |
| 3 | 38 | 45 | 100 | |
| 4 | 36 | 37 | 100 | 79 |
| 5 | 48 | 55 | 100 | |

TABLE 1-continued

| Compound | Column 1<br>% inhibition of carrageenan oedema at 2.5 mg/kg orally | Column 2<br>% inhibition of cyclooxygenase at $1 \times 10^{-5}$ mol/l | Column 3<br>% inhibition of lipoxygenase at $1 \times 10^{-5}$ mol/l | Column 4<br>% inhibition of aggregation of PMN at $1 \times 10^{-4}$ mol/l |
|---|---|---|---|---|
| 6 | 39 | 65 | 100 | 77 |
| 7 | 32 | 65 | 100 | 49 |
| 8 | 41 | 72 | 100 | 34 |
| 9 | 25 | 89 | 100 | 100 |
| 10 | 45 | 89 | 100 | 95 |
| 11 | 45 | 50 | 80 | 36 |
| 12 | 39 | 38 | 100 | 72 |
| 13 | 48 | | 100 | |
| 14 | 49 | | 100 | |

The present invention includes pharmaceutical formulations which, in addition to non-toxic, inert, pharmaceutically suitable vehicles, contain one or more active compounds according to the invention, or which consists of one or more active compounds according to the invention, and processes for the preparation of these formulations.

The present invention also includes pharmaceutical formulations in dosage units. This means that the preparations are in the form of individual parts, for example tablets, coated tablets, capsules, pills, suppositories and ampoules, of which the content of active compound corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert, pharmaceutically suitable vehicles there are to be understood solid, semi-sold or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical formulations.

Tablets, coated tablets, capsules, pills and granules can contain the active compound or compounds alongside the customary vehicles such as fillers and extenders (for example starches, lactose, sucrose, glucose, mannitol and silica), binders (for example carboxymethylcellulose, alginates, gelatin and polyvinylpyrrolidone), humectants (for example glycerol), disintegrants (for example agar-agar, calcium carbonate and sodium bicarbonate), solution retardant (for example paraffin) and absorption accelerators (for example quaternary ammonium compounds), adsorbents (for example kaolin and bentonite) and lubricants (for example talc, calcium and magnesium stearate and solid polyethylene glycols) or mixtures of the substances mentioned.

The tablets, coated tablets, capsules, pills and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned vehicles, can also be in a microencapsulated form to achieve a retard effect.

Suppositories can contain, in addition to the active compound or compounds, the customary water-soluble or water-insoluble vehicles, for example polyethylene glycols, fats, for example cacao fat, and higher esters (for example $C_{14}$-alcohol with $C_{16}$-fatty acid) or mixtures of these substances.

Ointments, pastes, creams and gels can contain the customary vehicles in addition to the active compound or compounds (for example animal and vegetable fats, waxes, paraffins, starches and tragacanth) or mixtures of these substances.

Powders and sprays can contain the customary vehicles in addition to the active compound or compounds (for example lactose, talc, silica and aluminum hydroxide) or mixtures of these substances. Sprays can additionally contain the customary propellants.

Solutions and emulsions can contain the customary vehicles in addition to the active compound or compounds, such as solvents, solubilizers and emulsifiers, for example water, ethyl alcohol, isopropyl alcohol, ethyl carbonate, ethyl acetate, benzyl alcohol, benzyl benzoate, propylene glycol, oils, in particular cottonseed oil, groundnut oil, corn germ oil, olive oil and sesame oil, glycerol, polyethylene glycols or mixtures of these substances.

For parenteral administration, the solutions and emulsions can also be in a sterile form which is isotonic with blood.

Suspensions can contain the custometry vehicles in addition to the active compound or compounds, such as liquid diluents (for example water, ethyl alcohol and propylene glycol), suspending agents (for example ethoxylated isostearyl alcohols, polyoxyethylene sorbitol and sorbitan esters, and microcrystalline cellulose) or mixtures of these substances.

The formulation forms mentioned can also contain colorants, preservatives and additives which improve the odour and flavour, for example peppermint oil and eucalyptus oil and sweeteners, for example saccharin.

The therapeutically active compound should preferably be present in the abovementioned pharmaceutical formulations in a concentration of about 0.1 to 99.5, preferably of about 0.5 to 95%, by weight of the total mixture.

The abovementioned pharmaceutical formulations can also contain other pharmaceutically active compounds in addition to the active compounds according to the invention.

The abovementioned pharmaceutical formulations are prepared in the customary manner by known methods, for example by mixing the active compound or compounds with the vehicle or vehicles.

The present invention also includes the use of the active compounds according to the invention and of pharmaceutical formulations which contain one or more active compounds according to the invention in human and veterinary medicine for the prevention, amelioration and/or cure of inflammatory processes in the human or animal body.

The active compounds or the pharmaceutical formulations can be administered cutaneously, orally, parenterally, intraperitoneally and/or rectally, preferably orally or cutaneously.

In general, it has proved advantageous in human medicine to administer the active compound or compounds in total amounts of about 0.1 to 200, preferably 0.1 to 70, mg every 24 hours, optionally in the form of several individual administrations, in order to achieve the desired results.

However, it can be necessary to deviate from the dosages mentioned and in particular to do so as a function of the nature and body weight of the subject to be treated, the nature and severity of the illness, the nature of the formulation and the administration of the medicament and the period or interval over which the administration takes place. Thus, it can suffice in some cases to manage with less than the abovementioned amount of active compound, while in other cases the abovementioned amount of active compound must be exceeded.

The particular required optimum dosage and the mode of administration of the active compounds can readily be decided by anyone skilled in the art on the basis of his expert knowledge.

The present invention is to be illustrated in detail by the examples which follow:

EXAMPLE 1

2-Allylamino-6-sulphamoyl-1,4-naphthoquinone (compound 12) was obtained, starting from 1,4-dioxo-1,4-dihydronaphthalene-6-sulphonic acid (Beilstein 11, (III), 622) by conversion into the sulphonamine followed by its reaction with allylamine in the presence of atmospheric oxygen (see Houben-Weyl, Methoden der Organischen Chemie (Methods of Organic Chemistry) 7/3a, 404 et seq.).

Melting point 222°–23° C.

EXAMPLE 2

2-Propionylamino-3-(2-methoxyethoxy)-1,4-naphthoquinone (compound 13)

15.2 g (0.1 mol) of 1,8-diazabicyclo[5.4.0]undec-7-ene in 50 ml of ethylene glycol monomethyl ether are added to a suspension of 26.35 g (0.1 mol) of 3-chloro-2-propionylamino-1,4-naphthoquinone in 100 ml of ethylene glycol monomethyl ether, and the mixture is stored at room temperature overnight. After cooling to 0° C., the mixture is filtered and the precipitate is thoroughly washed with cold methanol. Yield: 19.3 g (64% of theory), melting point 116°–17° C.

EXAMPLE 3

2-Acetylamino-3-ethoxy-1,4-naphthoquinone (compound 14) is obtained in a manner analogous to compound 13, from 3-chloro-2-acetylamino-1,4-naphthoquinone (Ber. Dtsch. Chem. Ges. 56, 1,291 (1923)) and ethanol. Yield: 56% of theory, melting point 155°–56° C.).

It will be understood that the specification and examples are illustrative but not limitative of the present invention and that other embodiments within the spirit and scope of the invention will suggest themselves to those skilled in the art.

We claim:

1. An anti-inflammatory composition in the form of a tablet, coated tablet, capsule, pill, suppository or ampule and comprising a diluent and an anti-inflammatory effective amount of a compound selected from the group consisting of

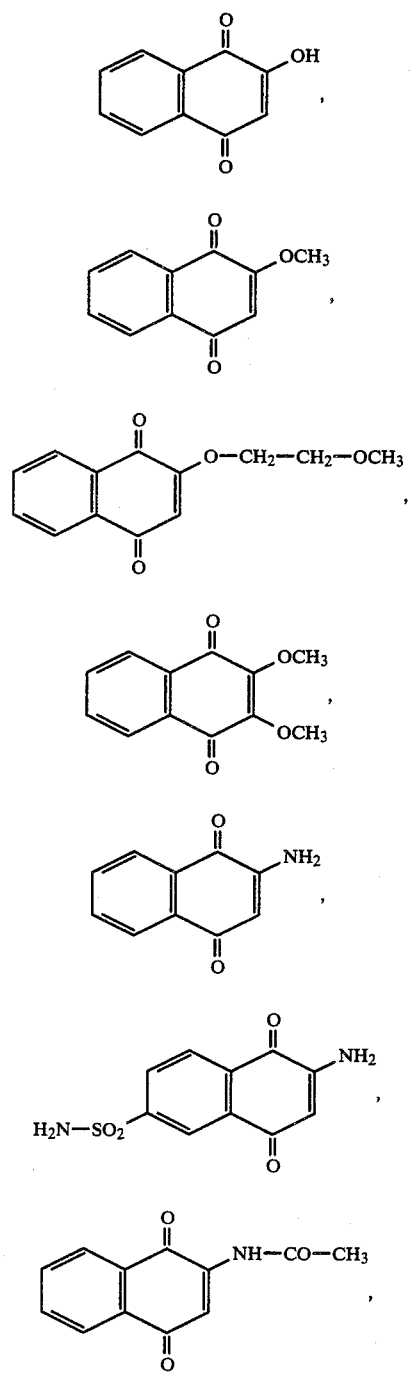

-continued

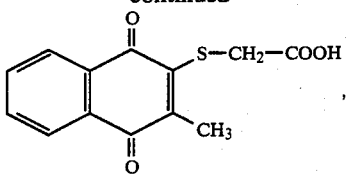

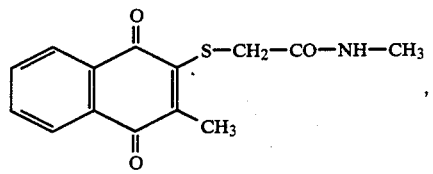

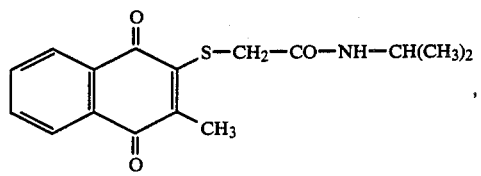

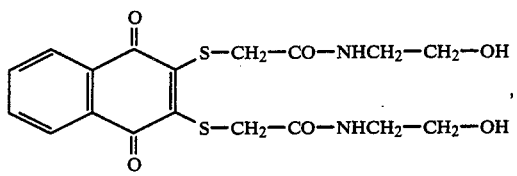

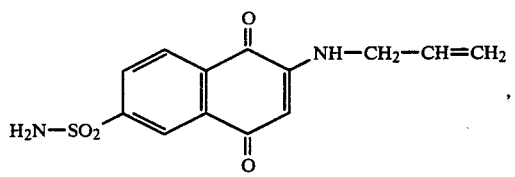

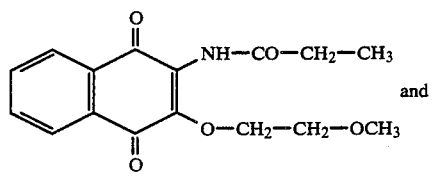

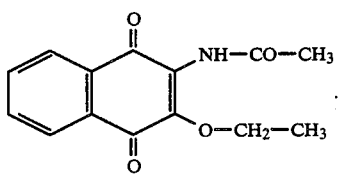

and

2. A composition according to claim 1, wherein such compound is 2-hydroxy-1,4-naphthoquinone of the formula

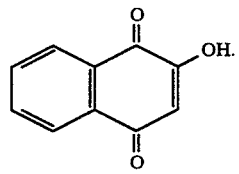

3. A composition according to claim 1, wherein such compound is 2-methoxy-1,4-naphthoquinone of the formula

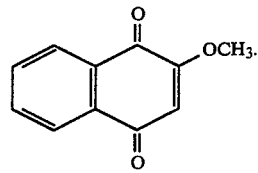

4. A composition according to claim 1, wherein such compound is 2-(2-methoxyethoxy)-1,4-naphthoquinone of the formula

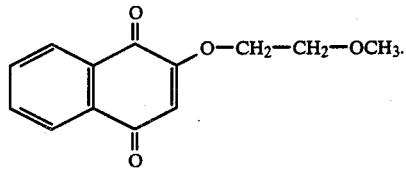

5. A composition according to claim 1, wherein such compound is 2,3-dimethoxy-1,4-naphthoquinone of the formula

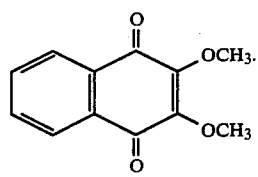

6. A composition according to claim 1, wherein such compound is ;b 2-amino-1,4-naphthoquinone of the formula

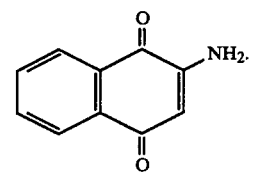

7. A composition according to claim 1, wherein such compound is 2-amino-6-sulphamoyl-1,4-naphthoquinone of the formula

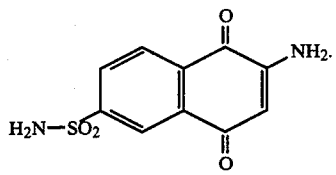

8. A composition according to claim 1, wherein such compound is 2-N-acetylamino-1,4-naphthoquinone of the formula

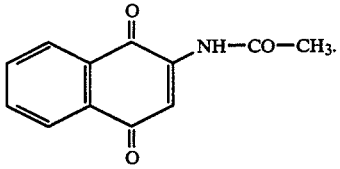

9. A composition according to claim 1, wherein such compound is 2-methyl-3-carboxymethylmercapto-1,4-naphthoquinone of the formula

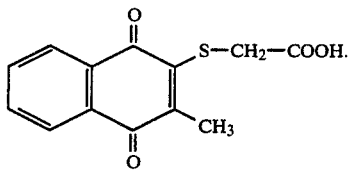

10. A composition according to claim 1, wherein such compound is 2-methyl-3-methylaminocarbonylmethylmercapto-1,4-naphthoquinone of the formula

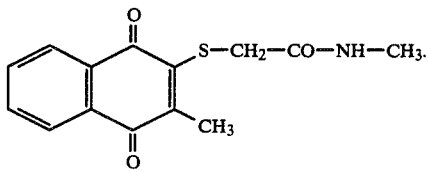

11. A composition according to claim 1, wherein such compound is 2-methyl-3-isopropylaminocarbonylmethylmercapto-1,4-naphthoquinone of the formula

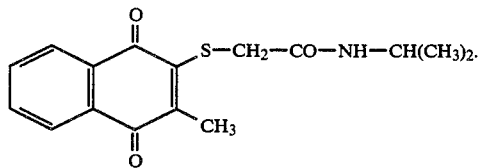

12. A composition according to claim 1, wherein such compound is 2,3-bis(2-hydroxyethylaminocarbonylmethylmercapto)-1,4-naphthoquinone of the formula

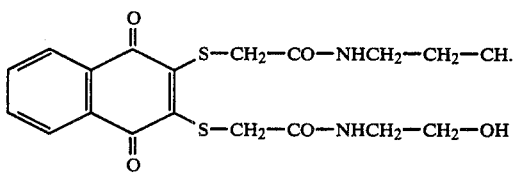

13. A composition according to claim 1, wherein such compound is 2-allylamino-6-sulphamoyl-1,4-naphthoquinone of the formula

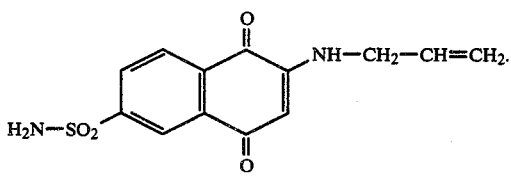

14. A composition according to claim 1, wherein such compound is 2-propionylamino-3-(2-methoxyethoxy)-1,4-naphthoquinone of the formula

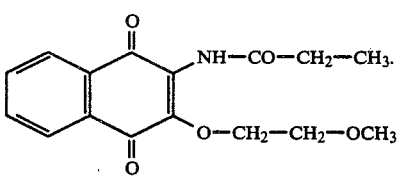

15. A composition according to claim 1, wherein such compound is 2-acetylamino-3-ethoxy-1,4-naphthoquinone of the formula

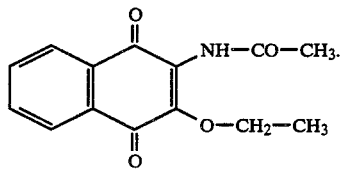

* * * * *